(12) United States Patent
Lavery et al.

(10) Patent No.: US 11,240,033 B2
(45) Date of Patent: Feb. 1, 2022

(54) SECURE DNA-BASED PASSWORD

(71) Applicant: International Business Machines Corporation, Armonk, NY (US)

(72) Inventors: Andrew J. Lavery, Austin, TX (US); Igor S. Ramos, Round Rock, TX (US); Silvia Giacone, Austin, TX (US); Bernadette Marie Wing, Spring Ranch, TX (US); Fernando Jose Suarez Saiz, Toronto (CA)

(73) Assignee: International Business Machines Corporation, Armonk, NY (US)

( * ) Notice: Subject to any disclaimer, the term of this patent is extended or adjusted under 35 U.S.C. 154(b) by 200 days.

(21) Appl. No.: 16/583,728

(22) Filed: Sep. 26, 2019

(65) Prior Publication Data

US 2021/0099302 A1   Apr. 1, 2021

(51) Int. Cl.
*H04L 29/06* (2006.01)
*H04L 9/32* (2006.01)
*G06F 21/46* (2013.01)
*G16B 15/00* (2019.01)
*G06F 21/62* (2013.01)

(52) U.S. Cl.
CPC ............ *H04L 9/3231* (2013.01); *G06F 21/46* (2013.01); *G06F 21/6209* (2013.01); *G16B 15/00* (2019.02); *H04L 9/3236* (2013.01)

(58) Field of Classification Search
CPC ..... H04L 9/0866; H04L 9/0861; H04L 9/088; H04L 9/3236; H04L 9/3231; G06F 21/32; G06F 21/46; G06F 21/6209; G16B 15/00
See application file for complete search history.

(56) References Cited

U.S. PATENT DOCUMENTS 9,270,446 B2   2/2016  Ayday et al.
2007/0041622 A1  2/2007  Salva Calcagno
(Continued)

FOREIGN PATENT DOCUMENTS

JP      2010020524 A    5/2019

OTHER PUBLICATIONS

Anonymous, "A biology specific method and apparatus to protect private genomics data stored in cloud %GTO," ip.com, An IP.com Prior Art Database Technical Disclosure, IP.com No. IPCOM000233288D, IP.com Electronic Publication Date: Dec. 5, 2013, 4 pages.

(Continued)

*Primary Examiner* — Thaddeus J Plecha
(74) *Attorney, Agent, or Firm* — Peter J. Edwards (57) ABSTRACT

A method includes determining a password-length threshold. The password-length threshold may comprise an integer. The method also includes obtaining, for a first user, a set of nucleotide locations. The number of nucleotide locations in the set may be greater than or equal to the integer. The method also includes obtaining a first sample of the user's DNA. The method also includes determining, in the first sample, a nucleotide at each nucleotide location in the set of nucleotide locations, resulting in a first nucleotide-password sequence. The method also includes performing a one-way hashing operation on the first nucleotide-password sequence with a first hashing algorithm, resulting in a first hashed password.

20 Claims, 6 Drawing Sheets

Specification includes a Sequence Listing.

(56) References Cited

U.S. PATENT DOCUMENTS

| | | | | |
|---|---|---|---|---|
| 2009/0110192 | A1* | 4/2009 | Elrod | H04L 9/0866 380/44 |
| 2014/0081665 | A1 | 3/2014 | Holmes | |
| 2014/0115341 | A1* | 4/2014 | Robertson | H04L 9/3228 713/183 |
| 2015/0169784 | A1* | 6/2015 | Anderson | H04L 69/329 707/756 |
| 2015/0254912 | A1 | 9/2015 | Weisman | |
| 2016/0072800 | A1 | 3/2016 | Soon-Shiong et al. | |
| 2016/0080384 | A1* | 3/2016 | Kermani | G16B 30/00 506/2 |
| 2016/0127379 | A1* | 5/2016 | Nayshtut | H04L 63/205 726/1 |
| 2018/0108019 | A1* | 4/2018 | Schneider | G06Q 20/023 |
| 2020/0076798 | A1* | 3/2020 | Lidsky | H04L 9/3231 |

OTHER PUBLICATIONS

Finnegan et al., "Identification and genomic data," PHG Foundation, Dec. 2017, 45 pages, ISBN: 978-1-907198-22-9.

Koepsell, "The Future of Genomic Data Encryption," EncrypGen, A Genomic Blockchain Network, Oct. 17, 2018, 7 pages.

"Epigenomics Fact Sheet," National Human Genome Research Institute, Last updated Apr. 1, 2016, Printed Aug. 29, 2019, 5 pages, https://www.genome.gov/27532724/epigenomics-fact-sheet/.

"What are single nucleotide polymorphisms (SNPs)?" Genetics Home Reference, Your Guide to Understanding Genetic Conditions, Published Aug. 20, 2019, 2 pages, https://ghr.nlm.nih.gov/primer/genomicresearch/snp.

Wong et al., "A longitudinal study of epigenetic variation in twins," epigenetics. Aug. 16, 2010, pp. 516-526, 18 pages, https://www.ncbi.nlm.nih.gov/pmc/articles/PMC3322496/.

Yousefi et al., "A SNP panel for identification of DNA and RNA specimens," BMC Genomics, Article No. 90, 2018, 4 pages, https://bmcgenomics.biomedcentral.com/articles/10.1186/s12864-018-4482-7.

Drahansky et al., "Influence of Skin Diseases on Fingerprint Recognition," Journal of Biomedicine and Biotechnology, vol. 2012, Article ID 626148, Feb. 26, 2012, 10 pages http://dx.doi.org/10.1155/2012/626148.

"Retinal scan," Wikipedia The Free Encyclopedia, Printed Sep. 25, 2019, 4 pages.

"Epigenetics," ThermoFisher Scientific, Printed Sep. 25, 2019, 2 pages.

"Three Optimized Workflows for CpG Island Methylation Profiling," Applied Biosystems, Dec. 2008 Publication 106AP24-01, 4 pages.

Kobalt, "Identifying Samples from Genomic Data," Printed Sep. 25, 2019, 8 pages http://massgenomics.org/2013/01/identifying-samples-genomic-data.html.

* cited by examiner

SEQUENCE LISTING

```
<160> NUMBER OF SEQ ID NOS: 1

<210> SEQ ID NO 1
<211> LENGTH: 17
<212> TYPE: DNA
<213> ORGANISM: Artificial Sequence
<220> FEATURE:
<223> OTHER INFORMATION: Example hypothetical genetic sequence or
      genome.

<400> SEQUENCE: 1
accgtcaaac ttccatt                                                17
```

SECURE DNA-BASED PASSWORD

SEQUENCE LISTING

A plain text file containing a sequence listing is incorporated by reference herein in its entirety. The name of the plain text file is 16_583728_SequenceListing. The date of creation of the plain text file is Jan. 3, 2020. The size of the plain text file is 483 bytes.

BACKGROUND

The present disclosure relates to protection of personal information, and more specifically, to development of secure, unique passwords.

Deoxyribonucleic acid (referred to herein as DNA) is a genetic code composed of, among other components, a sequence of nucleotides. Each nucleotide includes one of four nucleobases: adenine (A), cytosine (C), guanine (G), and thymine (T). The pattern of nucleobases in the sequence of nucleotides (e.g., cytosine, thymine, thymine, guanine, cytosine, or "CTTGC") is the primary feature that encodes an organism's genetic code. For this reason, nucleotides are often identified based on the nucleobase it contains, a sequence of DNA is often described by the sequence of nucleotides identified by those nucleobases.

A person's complete DNA sequence is unique to the point that it can differentiate that person from any other person on earth, except for clones of that person and some close relatives (e.g., identical twins). Identifying a sufficient amount of the unique variation in a person's genome is one method of using a person's DNA sequence to identify that person. For example, a genetic variation in which a single nucleotide is switched to a different nucleotide is called a single-nucleotide polymorphism (referred to herein as "SNPs"). The locations of many SNPs that are common throughout the human population are known, but the nucleotide at each SNP location may vary from person to person due to the random nature of genetic variations.

As noted, if two people have identical DNA sequences (e.g., identical twins), identifying the sequence of the nucleotides in each person's genome is not sufficient to differentiate between those two people. However, epigenetics may often be used to differentiate even between individuals with identical DNA sequences. Epigenetics involves molecular changes to a nucleobase in a person's genome due to that person's environmental exposure. For example, some cytosine nucleotides, when followed in a person's genome by a guanine nucleotide, may exhibit methylation as a result of environmental exposure. If a first person's genome exhibits methylation at a particular CG sequence and a second person's genome does not, the methylation at that location can be used to differentiate the first person and the second person.

SUMMARY

Some embodiments of the present disclosure can also be illustrated as a method comprising determining a password-length threshold. The password-length threshold may include an integer. The method may also include obtaining, for a user, a set of nucleotide locations. The number of locations in the set may be greater than or equal to the integer. The method may also include obtaining a sample of the user's DNA. The method may also include determining, in the sample, a nucleotide at each nucleotide location in the set of nucleotide locations. This may result in a nucleotide-password sequence. The method may also include performing a one-way hashing operation on the nucleotide-password sequence with a hashing algorithm. This may produce a hashed password.

Some embodiments of the present disclosure can also be illustrated as a system comprising a first sequencer configured to perform a first method, which may include obtaining a password-length threshold. The password-length threshold may include an integer. The number of locations in the set may be greater than or equal to the integer. The method may also include obtaining a sample of the user's DNA. The method may also include determining, in the sample, a nucleotide at each nucleotide location in the set of nucleotide locations. This may result in a nucleotide-password sequence. The method may also include performing a one-way hashing operation on the nucleotide-password sequence with a hashing algorithm. This may produce a hashed password.

Some embodiments of the present disclosure can also be illustrated as a computer program product that comprises a computer readable storage medium having program instructions embodied therewith. The instructions may be executable by a computer to cause the computer to receive, from a first sequencer, identification information associated with a first user. The instructions may also cause the computer to transmit, to the first sequencer, a set of nucleotide locations and a set of hash information. The instructions may also cause the computer to receive, from the first sequencer, a first hashed password. The instructions may also cause the computer to store, in a profile for the first user, the set of nucleotide locations, the set of hash information, the identification information, and the hashed password.

The above summary is not intended to describe each illustrated embodiment or every implementation of the present disclosure. The method may also include obtaining, for a user, a set of nucleotide locations.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to protection of personal information, more particular aspects relate to development of secure, unique passwords. While the present disclosure is not necessarily limited to such applications, various aspects of the disclosure may be appreciated through a discussion of various examples using this context.

In various industries, services delivered to a person may require disclosure of sensitive information belonging to that person. For example, when a person visits a medical provider or engages in a real-estate transaction, the medical provider or parties to the transaction may require sensitive personal information that can be used to identify that person. This information may include, for example, social security number, medical history, financial history, criminal history, and others. While this information may be necessary to complete some services, it is important to many individuals that their sensitive personal information only be distributed with their explicit consent.

However, in instances of identity theft, it can be possible for an identity thief to fraudulently give consent to the distribution of another person's personal data. That personal data may then be used to further impersonate that person or otherwise profit off that person's identity. In some instances, personal passwords and passphrases can be used to prevent an identity thief from fraudulently giving consent, but oftentimes personal passwords are stored insecurely or are easily guessed by identity thieves. In some instances, unique identifiers, such as social security numbers, may be used to identify a person for consent purposes, but identifiers such as social security numbers are often hacked and stolen themselves. Finally, biometric information may sometimes be used to identify a person giving consent, such as using retinal or fingerprint scans. However, biometric information can change frequently through a person's lifetime due to environmental exposure, disease, injury, or other health conditions. Thus, relying solely on biometric information may increase the risk of false negatives and inability of a person to access his or her personal information or give consent for that personal information to be distributed.

As an alternative, it is theoretically possible to utilize a person's DNA (e.g., genomic sequence) to uniquely identify that person. However, typical methods of identifying a person by that person's DNA include storing that person's genomic information for comparison. This results in a potentially significant security risk. If the server storing the person's genomic information were hacked, that person's genomic information may be stolen by an identify thief. In many instances, the potential damage resulting from the theft of one's unique DNA information may be greater than the potential damage resulting from fraudulent consent to distribute personal data that the DNA verification was intended to protect. Therefore, while typical DNA verification methods may be effective, the risk that DNA verification carries may make them more hazardous than worthwhile.

Some embodiments of the present disclosure present a secure, DNA based password system that can be used to provide user consent. In some embodiments, the drawbacks of other consent systems, such as passwords being stolen or forgotten, unique identifiers being stolen, transience of biometric information, and sensitivity to DNA theft, are addressed. In this way, some embodiments of the present disclosure provide for a DNA based password system that does not require long-term storage (e.g., storage that last longer than 5 minutes) of a person's DNA information.

In some embodiments of the present disclosure, a user is given access to a sequencer device that is configured to encrypt a specific sequence of the user's DNA into a hash code using a one-way hash function. This specific sequence may be composed of single nucleotides from throughout the user's genome. The locations of the specific nucleotides (sometimes referred to herein as the "nucleotide locations") in the sequence may be selected from a list of common single-nucleotide polymorphisms (referred to herein as "SNPs"), epigenetic variations sites, or both. A list of SNPs, for example, may take the form of a list of SNPs in hypervariable regions of the genome. A list of epigenetic variations, for example, may take the form of a list of methylation-base modification at cytosine-guanine sequences. For example, in some embodiments the nucleotide locations may take the form of an RS number (also referred to as an "RS id or an RS code") (e.g., rs1234567), each of which identifies the location of a specific, known SNP. However, any form of addressing specific nucleotides that is consistent with the embodiments of this disclosure may be utilized.

Once the nucleotide locations are selected, the sequencer may process the user's DNA to determine which nucleotides (e.g., adenine, cytosine, guanine, thymine) are found at the selected locations (and, if applicable, whether one or more of those nucleotides have been methylated). These nucleotides may then be combined into a sequence of characters representing the selected nucleotides, which may be referred to herein as a "sequence password." For example, a sequence password that is 5 nucleotides in length may be represented as: "AACTG."

In some embodiments, a sequence password may be composed solely of a characters that represent the nucleobases in the corresponding nucleotides. In other embodiments, the sequence password may also include characters that represent epigenetic information for those nucleotides. For example, in some embodiments each nucleotide in the sequence password may have an attached character that states whether the nucleotide is methylated. This character may, for example specify that the nucleotide is methylated, partially methylated, or non methylated, and may be attached to different nucleotides in different embodiments.

In some embodiments, for example, this character may be appended only to cytosine nucleotides that are followed by a guanine nucleotide in the user's genome. In these embodiments, the earlier 5-nucleotide sequence password may be represented as, for example, "AACmTG" if the "cytosine" nucleotide corresponding to the sequence password is methylated in the user's genome. In some such embodiments "Cm" may be used as a data-efficient representation for specific or formal nomenclature, such as "5mC," which may refer to methylation of the number 5 carbon of a cytosine ring. In some embodiments, a sequence password may also be appended with formal nomenclature, but these embodiments may be less data efficient (in other words, require more bits, bytes, or characters to store the password). In other embodiments, for example, the character may be appended to all nucleotides in the sequence password. In these embodiments, nucleotides or nucleotide sequences for which epigenetic alteration is not known to be applicable may be appended with a character that signifies "non-methylated," "not applicable," "NULL," or other similar descriptors in accordance with the embodiments of the present disclosure. For example, the earlier 5-nucleotide password may be represented as "AnAnCpTnGn" if the "cytosine" nucleotide is partially methylated in the user's genome.

In some embodiments, it may be possible to encode epigenetic methylation in a password without adding characters. For example, to express whether a cytosine nucleotide is methylated, partially methylated, or non methylated, a sequence password may express the cytosine nucleotide with a letter "m," "p," or "n" respectively. For example, if the cytosine nucleotide in the earlier 5-nucleotide sequence password were methylated, the sequence password may be represented as "AAmTG." However, if the cytosine nucleotide were non methylated, the sequence password may be represented as "AAnTG."

After the sequence password is obtained, it may be hashed with a hash function, which may include appending a cryptographic salt to the sequence password. This cryptographic salt may be a random value that is added to the sequence password to increase the random, unique nature of the result of the hash function. Collectively, the hash function and the cryptographic salt (if used) may be referred to as the "hash information" (also referred to herein as the "hash info"). Hashing the sequence password would transform the sequence password into a hash (sometimes referred to herein as a "hashed password," or "hash result"). This hash password may reflect the nucleotides in the sequence password as well as any epigenetic information encoded by the password.

Once the hashed password is obtained, the hashed password, the nucleotide locations, and the hash information may be stored in one or more a secure locations, while the user's genome and sequence password may be securely deleted. By deleting the genome and sequence password, the embodiments of the present disclosure may significantly decrease the risk that a user's genomic information is compromised. For example, even if the one or more secure locations is hacked by an identity thief, the thief may be unable to steal anything other than the nucleotide locations (i.e., information that maps to a set of locations in any person's genome), hash information, and a hash result.

Further, if the hash function is a one-way hash function, the identity thief may be unable to determine the sequence password (i.e., the nucleotides in a person's genome at the nucleotide locations) without manually hashing all possible nucleotide sequences with the hash information and comparing the result with the hashed passwords. However, in many instances, the amount of possible nucleotide passwords to transform with the hash function may make this determination infeasible. For example, if the sequence password were 10 characters long and did not include any epigenetic information, there would be 1,048,576 possible combinations of characters (10 characters that can each be an "A," "C," "G," or "T,"). However, if epigenetic information were encoded in the password, the possible combinations could be significantly higher. For example, if a "cytosine" could be encoded as a "C" (for cytosine nucleotides that are not followed by a "guanine" in the user's genome), an "m" (for cytosine nucleotides that are methylated), an "n" (for cytosine nucleotides that are non methylated), or a "p" (for cytosine nucleotides that are partially methylated), a 10-character password would have 282,475, 249 combinations.

Finally, even if an identify thief did manage to hack the one-or-more secure locations and spend the time and resources to determine, by trial and error, the sequence password, it would only provide the thief with the "identities" of 10 nucleotides of the user's entire genome of over 3 billion nucleotides. The exposure of such a small percentage of a user's genome is unlikely to result in any risk to the user, even if exposed to an identity thief.

In some embodiments, the embodiments of the present disclosure may be used to create a secure consent network between multiple businesses a user visits. The consent network may be run by a secure third-party entity that may provide equipment to businesses to participate in the network. For example, a user may visit a first business that collects sensitive information about that user. This business may be, for example, a medical provider or a financial advisor. The business may license a genetic sequencer from the third-party entity and may use the sequencer to sequence a part or all of the user's genome (e.g., through blood, hair, or saliva samples). The sequencer may obtain a sequence password length, set of nucleotide locations, or both, from a remote secure server operated by the secure network and identify the user's nucleotides at those locations. In some embodiments, the sequencer may also obtain hash information from the secure server to enable the sequencer to transform the sequence password to a hashed password. In other embodiments, the sequencer may create a random hash function and cryptographic salt. In some embodiments, the sequencer may obtain either a hash function or cryptographic salt from the secure server and create the other (for example, the sequencer may obtain a hash function and create a random cryptographic salt). Upon developing the hashed password, the sequencer may delete any remaining genomic information (e.g., the sequence password and the user's genome) and transmit the hashed password and, in some embodiments, the hash information to the secure server.

Continuing the example, if the user then visits a second business that participates in the secure network, the business may request the user's information from the first business (for example, a user's real-estate title company may request information from the user's previous real-estate title company, or the user's dentist may request information from the user's previous dentist). The first business may inform the second business that it participates in the secure consent network, and request that the second business confirm the user's identify and consent with the secure server. A second sequencer licensed to the second business by the secure network may then obtain the previously used nucleotide locations and hash information from the secure server. The second sequencer may then sequence the user's genome, identify the nucleotides at the provided nucleotide locations, develop a sequence password, and use the hash information to transform the sequence password to a second hashed password. The second sequencer may then transmit that second hashed password to the secure server, which may compare the second hashed password to the previous hashed password (i.e., the hashed password created by the first sequencer). If the hashed passwords match, the secure server may inform the first business and second business of the hash match. In some embodiments, this hash match may provide the necessary consent for the first business to transmit the user's information to the second business.

Figure 1:
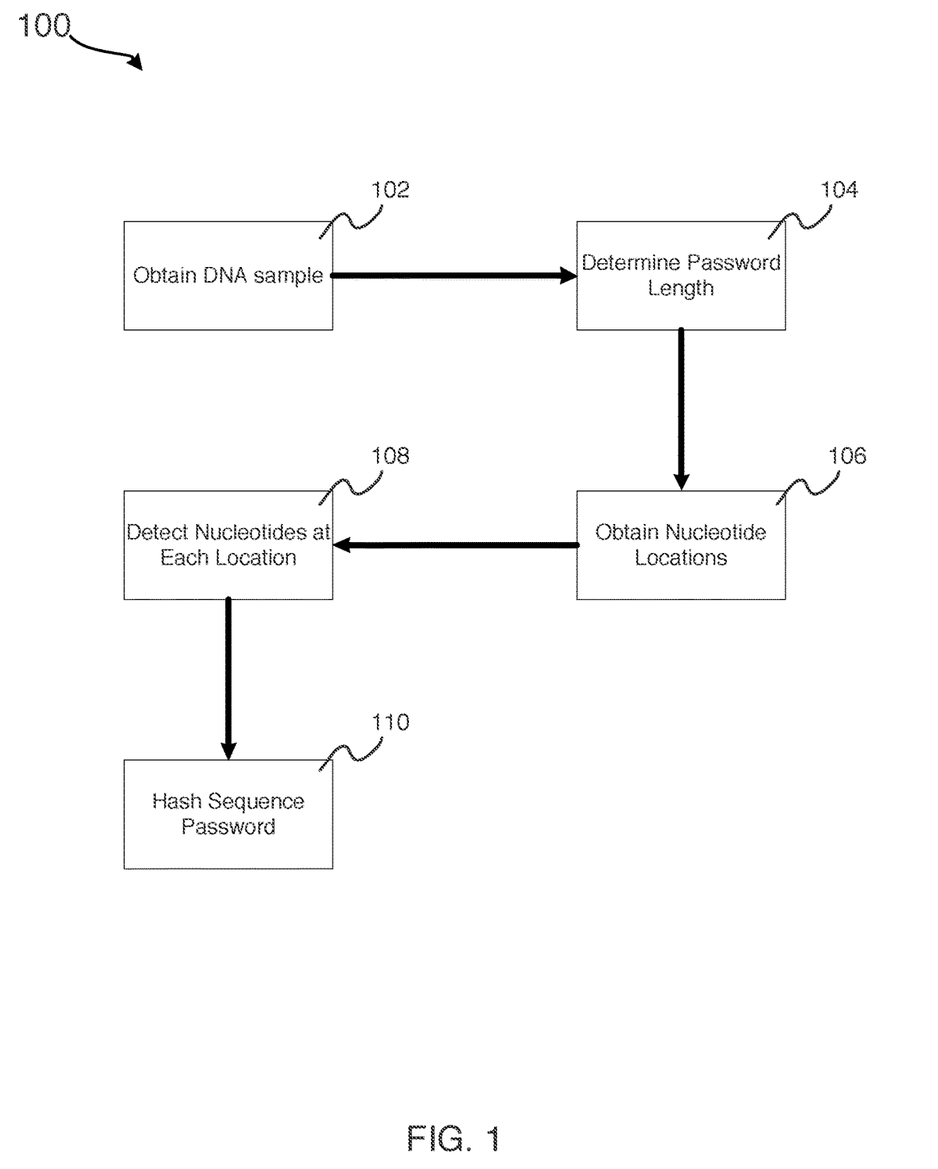
FIG. 1 depicts an example method by which a DNA-based hashed password is created, in accordance with embodiments with the present disclosure.

FIG. 1 depicts an example method 100 by which a DNA-based hashed password is created. Method 100 may be performed by a sequencer that is, for example, licensed to a user or a business by a secure-password or secure-consent network. In block 102, the sequencer obtains a sample of the user's DNA. This may include, for example, taking a hair sample from the user, taking a skin sample for the user, or taking a drop of blood from the user. The sequencer may then determine the desired number of characters (i.e., the length) of a sequence password (e.g., the number of nucleotide locations encoded in the sequence password) in block 104. In some embodiments, this password length may be provided to the sequencer by the user. In other embodiments, this password length may be provided to the sequencer by a business the user is visiting. In some embodiments, the password length may be obtained from a secure server that is run by a secure password/consent network.

In some embodiments, the password length may take the form of a number of characters (e.g., "5 characters"). However, in other embodiments the password length may also provide for restrictions on the password. For example, a user may specify that the password be 8 characters long, but the password contain at least one character that encodes the methylation of a cytosine nucleotide that is followed by a guanine nucleotide in the user's genome. In some embodiments, the password length may take the form of a threshold. For example, the password length may establish a minimum number of characters that a sequence password must contain (e.g., 10 or more characters). In some such embodiments, any password length equal to or above the threshold may be used.

In block 106, the nucleotide locations for the password are determined. In some embodiments, for example, a sequencer may randomly select a number of known RS IDs that is equal to the password length determined in block 104. In some embodiments, the sequencer may select a mix of nucleotides located at RS IDs and nucleotides located at common epigenetic sites (e.g., cytosine-guanine pairs that are known for common methylation in a population), resulting in a mix of characters that is equal to or greater than the password length. In some embodiments, the nucleotide locations obtained in block 106 may be obtained from a remote secure server (e.g., a server operated by a third party that licenses the sequencer to the user/business).

In some embodiments, block 104 and block 106 may effectively be performed simultaneously. For example, in some embodiments, a list of nucleotide locations could be provided to a sequencer by a remote server. This list of nucleotide locations could also, in effect, provide the password length, because it could tell the user the exact number of nucleotides to contribute to the sequence password. For example, if a user is sent a list of 8 nucleotide locations, the password length may be established at 8 characters (or at least 8 characters).

After nucleotide locations are obtained in block 106, the sequencer analyzes the DNA sample obtained in block 102 and detect the nucleotides at each obtained location (for example, the sequencer may identify the nucleobase of the nucleotide located at each nucleotide location). These nucleotides may then be combined into a sequence password.

In some embodiments, the user's DNA sample may be discarded as soon as block 108 is completed, reducing the likelihood that the user's DNA could be compromised. In fact, in some embodiments the DNA sample may not be obtained until the nucleotide locations are discovered in block 106. For example, block 102 and block 108 may occur simultaneously once the target nucleotide locations are obtained. In these embodiments, a tissue sample may be processed and nucleotide information may only be stored transiently. For example, a sequencer may only store nucleotide information for nucleotide locations obtained in block 106. All other nucleotide information may be overwritten immediately.

The sequencer hashes the sequence password in block 110. In some embodiments, block 110 may include obtaining a hashing function and cryptographic salt from a remote server. In other embodiments, block 110 may include creating a random hashing function and cryptographic salt. The hashing function in block 110 results in a hashed password.

In some embodiments, this hashed password may be utilized to confirm a user's identity in lieu of (or in addition to) other credentials. For example, a user may store a copy of a hashed password on a user's computer, or submit the hashed password to a website. In these examples, the user may have access to a sequencer that is capable of performing method 100. This sequencer may also be capable of communicating with a user device (e.g., a phone or computer) through, for example, a wired or wireless communication protocol (e.g., USB or Bluetooth). In these examples, hash information and nucleotide locations used to create the hashed password may either be located on the user's sequencer or on the user's computer or by the entity that operates the website. When the user wishes to access his/her computer, for example, the sequencer may request the hash information and nucleotide locations from his/her computer and request that the user provide tissue sample to the sequencer. The sequencer may then perform blocks 108 and 110 of method 100 and submit the resulting hashed password to the computer, which could compare the hashed password to the previously stored hashed password. In other examples, the sequencer may store the hash information and nucleotide locations, and the sequencer may transmit a hashed password to a website that the user is attempting to access. The website may then compare the hashed password to a previously submitted hashed password, and allow the user to access, for example, the user's portal on the website in the case of a hash match.

Figure 2:
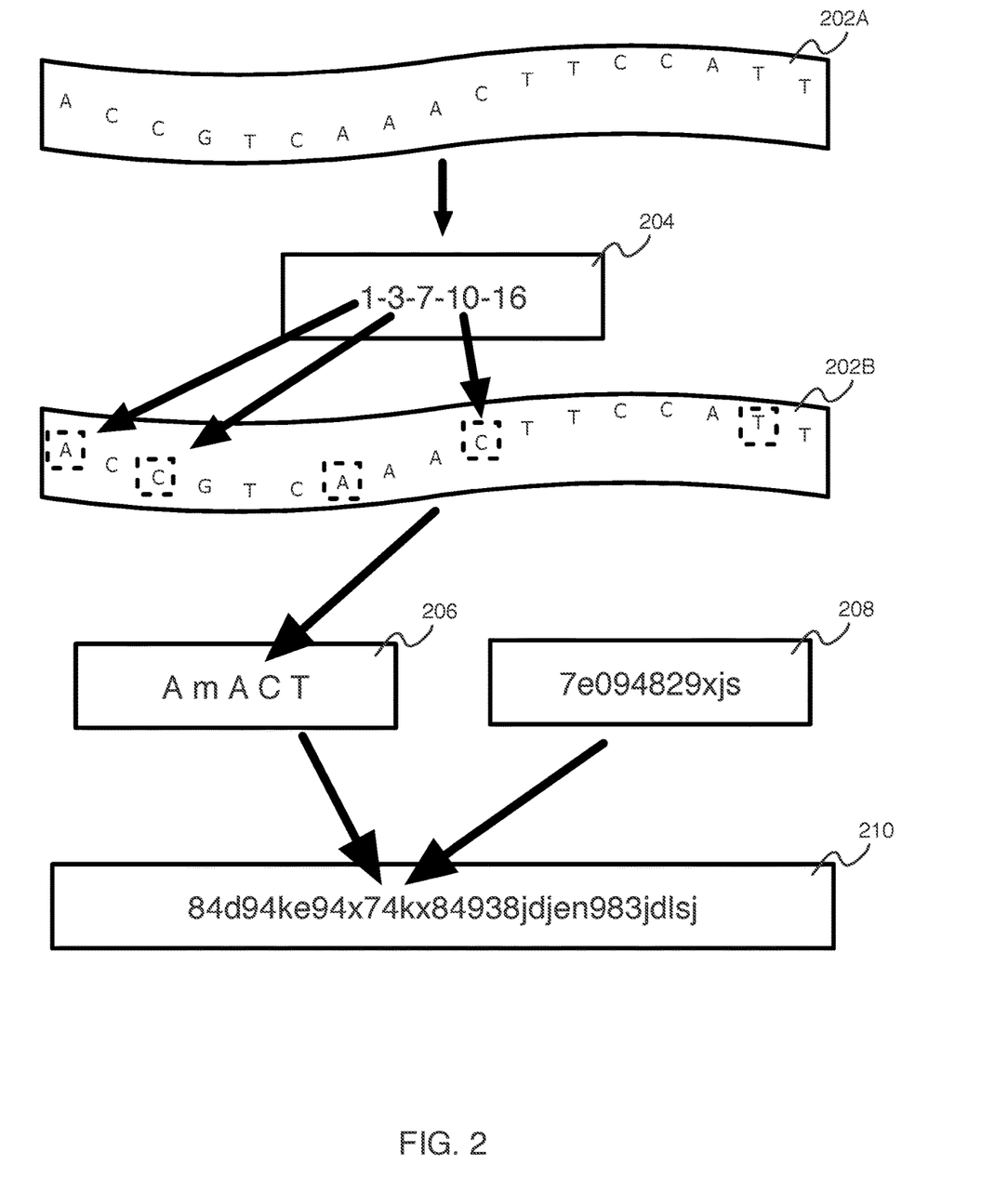
FIG. 2 illustrates an example flowchart of the transformation of a segment of DNA to a hashed password, in accordance with embodiments with the present disclosure.

FIG. 2 illustrates an example flowchart of the transformation of a segment of DNA 202A to a hashed password. FIG. 2 is presented as an abstraction solely for the purpose of explanation—the scale, characters, and other aspects of the presentation are not necessarily intended to resemble actual use-case features. In FIG. 2, DNA sample 202A represents a user's genome, and contains the DNA segment "A C G T C A C T C A T," (SEQ ID NO: 1) consisting of 17 nucleotides. In some embodiments of the present disclosure, this DNA segment may represent the user's entire genome that is sequenced by a sequencer licensed to a user or a business. In other embodiments, this DNA segment may only represent a portion of a user's genome (e.g., a section of a chromosome that contains a high percentage of SNPs).

Nucleotide locations 204 represent a list of nucleotide locations that a sequencer may obtain from a remote server. Nucleotide locations 204 may, for example, be used when developing a hashed password initially (such as when a user first visits a cardiologist that participates in a secure-consent network), or when creating a subsequent hashed password to compare to an initial hashed password (such as when a user visits a new cardiologist and consents to the new cardiologist obtaining medical records from the user's prior cardiologist). As illustrated, nucleotide locations 204 are illustrated as six Arabic numerals that correspond to the order of the nucleotides from left to right in DNA sample 202A. However, in practice nucleotide locations could take various forms that could be used to identify the location of a nucleotide in a user's genome.

DNA sample 202B is illustrated below nucleotide locations 204, and represents a view of DNA sample 202A with the nucleotide locations specified by nucleotide locations 204 outlined by a dotted line. For example, adenine, encoded in DNA sample 204B by a letter "A" occupies the first DNA address and the first nucleotide location. Cytosine, encoded in DNA sample 204B by a letter "C" occupies the third DNA address and the second nucleotide location. Further, because this cytosine is followed in the user's genome by a guanine nucleotide, it is a candidate for epigenetic methylation. By contrast, the nucleotide in the tenth DNA address and the fourth nucleotide location is not followed by a guanine nucleotide in the user's genome. For this reason, the cytosine that is found at the tenth DNA address is unlikely to be a candidate for cytosine methylation.

Sequence password 206 is obtained by adding the nucleotides found at the locations identified by nucleotide locations 204 to a password sequence. As illustrated, this represents a 5-character password length. Further, as illustrated, the first, third, fourth, and fifth characters represent the first letters of the corresponding nucleotides at the corresponding DNA addresses. However, the second character, a lower-case "m," represents a methylated cytosine.

Cryptographic salt 208 may be combined with sequence password 206 when transforming sequence password 206 into a hashed password. In some embodiments, for example, cryptographic salt 208 could be appended to the beginning or end of sequence password 206 (e.g., "AmACT7e094829xjs"). The sequence password, with the cryptographic salt, may then be hashed by a hash function, resulting in hashed password 210. Hashed password 210 may then be utilized in a process that, for example, confirms the user's identity or provides the user's consent consistent with the embodiments of the present disclosure.

Figure 3:
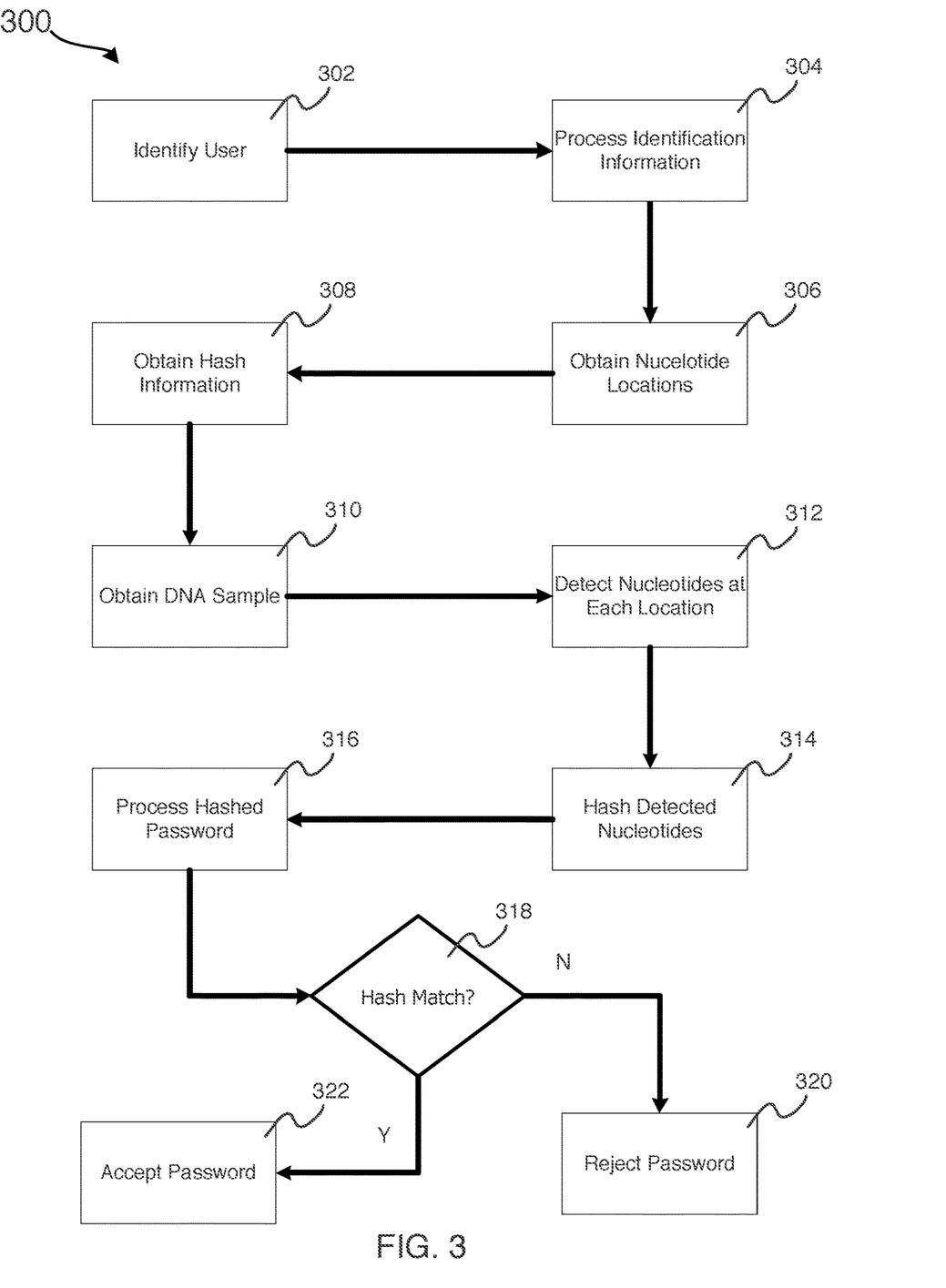
FIG. 3 depicts an example method of creating a DNA-based hashed password and comparing it to a previously created hashed password, in accordance with embodiments with the present disclosure.

Such an embodiment is illustrated by FIG. 3, depicts an example method 300 of creating a DNA-based hashed password and comparing it to a previously created hashed password. Method 300 may be performed after a first hashed password had been created (for example, by method 100). Method 300 may be performed in whole or in part, for example, by a sequencer that is licensed to an organization that participates in a secure consent network. For example, a user's bank may keep a sequencer at each branch location to confirm a user's identity and password before transferring money out of a user's account.

In block 302, the user is identified. In some embodiments, the nature of the information by which the user is identified may depend upon the identification information that is associated with the user's previously created hashed password. For example, in some embodiments, a user may have a specific user ID that the user enters into a display on the sequencer before uploading a DNA sample. Similar to logging on to a portal on a website, for example, the user ID may be the user's login name, and the hashed password may be the user's login password. In other embodiments, block 302 may simply include determining the legal name connected with a user account. Continuing with the prior example of a user visiting a bank branch, this legal name may be the legal name associated with the user's bank account.

In some embodiments, the identity information obtained in block 302 may include biometric information. For example, in some embodiments a user visiting a doctor's office may sign in by providing a hair sample, or a user signing in on a computer device to a website may provide a fingerprint to a fingerprint reader on that computer device. In some embodiments, this biometric information may be in addition to, rather than in lieu of, other identity information. Continuing with the prior bank-account example, the user may provide a user ID to a sequencer, at which point the sequencer may scan the user's retina to increase the confidence that the person providing the user ID is indeed the owner of the associated bank account.

In block 304, the identity information obtained in block 302 is processed. In some embodiments, processing the identity information may involve a sequencer with which the user is interacting searching a database for a secure-password account associated with the identity information. For example, the sequencer may determine whether a secure-consent network contains a hashed password, hash information, and nucleotide locations associated with the identity information obtained in block 302.

In some embodiments, processing the user's identification information in block 304 may include the sequencer transmitting the identification to another machine in a secure-consent network. For example, in some embodiments it may be beneficial to store all user information in a remote, secure server. In some of these embodiments, block 304 may transmit the obtained user information to that secure server. In some embodiments, the user's password information may be stored with a second sequencer licensed by a third-party, in which case block 304 may include transmitting the obtained identity information to that second sequencer. For example, if the user is closing on a new house, the user's accountant may require user consent before sending financial information to a title company associated with the transaction. In this example, a sequencer at the title company may transmit, in block 304, the identify information obtained in block 302 to another sequencer at the user's accountant's firm.

In block 306, the sequencer performing method 300 obtains the nucleotide locations that were used to create the previously established hashed password for the user (for example, through method 100). In some embodiments, these nucleotide locations may be acquired from a storage unit located on the sequencer, from a secure server (e.g., a remote server operated by a secure-consent network), or from another sequencer. In some embodiments, the nucleotide locations may take the form, for example, of known locations of SNPs, of locations of common epigenetic variations, or others.

In block 308, the sequencer performing method 300 obtains the hash information (e.g., a hash algorithm and cryptographic salt) that was used to create the previously established hashed password for the user (for example, through method 100). In some embodiments, these nucleotide locations may be acquired from a storage unit located on the sequencer, from a secure server (e.g., a remote server operated by a secure-consent network), or from another sequencer.

In some embodiments, operations 306 and 308 may be performed simultaneously. For example, a sequencer performing method 300 may obtain nucleotide locations and hash information at the same time from a remote server. In other embodiments, they may occur in the sequence shown or in the reverse sequence. In some embodiments, the nucleotide locations and hash information may be obtained from different sources (e.g., the hash information may be stored locally on the sequencer, but the nucleotide locations may be stored in a remote server or a remote sequencer).

In block 310, the sequencer obtains a sample of the user's DNA. This may include previously discussed methods of sampling DNA in accordance with the embodiments of the present disclosure. For example, a user could bring in a vial of blood that the user drew before visiting the user's bank branch. However, to avoid potential fraud, it may be beneficial for the user to provide a DNA sample on site (e.g., with a hair sample).

In block 312, the sequencer detects the nucleotides in the obtained DNA sample that are located at the locations obtained in block 306. This may be performed, for example, by methods associated with block 108 of method 100 or associated with 204, 202B, and 206 of FIG. 2. In some embodiments, the detected nucleotides may be combined into a sequence password. Once the nucleotides are detected in block 312, the detected nucleotides are hashed in block 314 using the hash information obtained in block 308. Block 314 may output a hashed password, as discussed in previous embodiments.

In block 316, the hashed password is processed. In some embodiments, this may include transmitting the hashed password to a remote location (e.g., a remote password server, a sequencer located at a third-party organization) to analyze. In some embodiments, block 316 may include locating the previously created hashed password for a password comparison (e.g., in the sequencer's storage). In other embodiments, block 316 may include requesting the previously created hashed password from a remote sequencer or secure server.

In block 318, the sequencer determines whether the hashed password matches the previously created hashed password. In embodiments in which the previously created hashed password is stored on the sequencer, the sequencer may perform the comparison. In embodiments in which the previously created hashed password is stored remotely, however, block 318 may include obtaining a notification of whether the passwords match or do not match from the remote location (e.g., a server operated by a secure-password or secure-consent network).

If the hashed password created in block 314 does not match the previously created hashed password, the hashed password is rejected in block 320. The operations in block 320 may depend on the use case in which method 300 is being employed. For example, in some embodiments the sequencer performing method 300 may display a hash mismatch, and may prompt the user to insert a new sample of DNA. This may be beneficial in case the first sample of DNA was contaminated or the sequencer incorrectly detected the nucleotides in block 312. In other embodiments, the sequencer could lock the user's account (e.g., a financial account) to prevent fraudulent access. In some embodiments, a notification could be sent to the user (e.g., through email, text message, phone call, or others) to alert the user that a failed attempt was made to access the user's account/information with an incorrect DNA sample.

On the other hand, if the hashed password created in block 314 does match the previously created hashed password, the password is accepted in block 322. The operations in block 322 may also depend on the use case in which method 300 is being employed. For example, in some embodiments method 300 may be performed to obtain user consent to a first medical provider sharing medical records with a second medical provider. In this example, the sequencer performing method 300 may be located at the second medical provider and may inform the first medical provider of the hashed-password match when requesting the medical records. In other embodiments, for example, the accepted password may simply allow the user to log into an account (e.g., on a web-page portal or to access a bank account at the user's bank branch).

Some embodiments of the present disclosure may include changing a user's hashed password periodically or upon the occurrence of a pre-determined event. For example, some embodiments may include changing the hashed password each time the user submits it (e.g., logs in using the password, submits the password as part of a consent to an information exchange or account modification, or others). For example, in some embodiments of method 300, a new set of nucleotide locations may be obtained after block 318, 320, or 322. Those nucleotide locations may completely or partially differ from the nucleotide locations used to create the previously created hashed password. In some embodiments, new hash information may also be obtained at this point. A new hashed password may then be created using the new set of nucleotide locations and hash information, and uploaded to a secure server, overwriting the previous hashed password.

Figure 4:
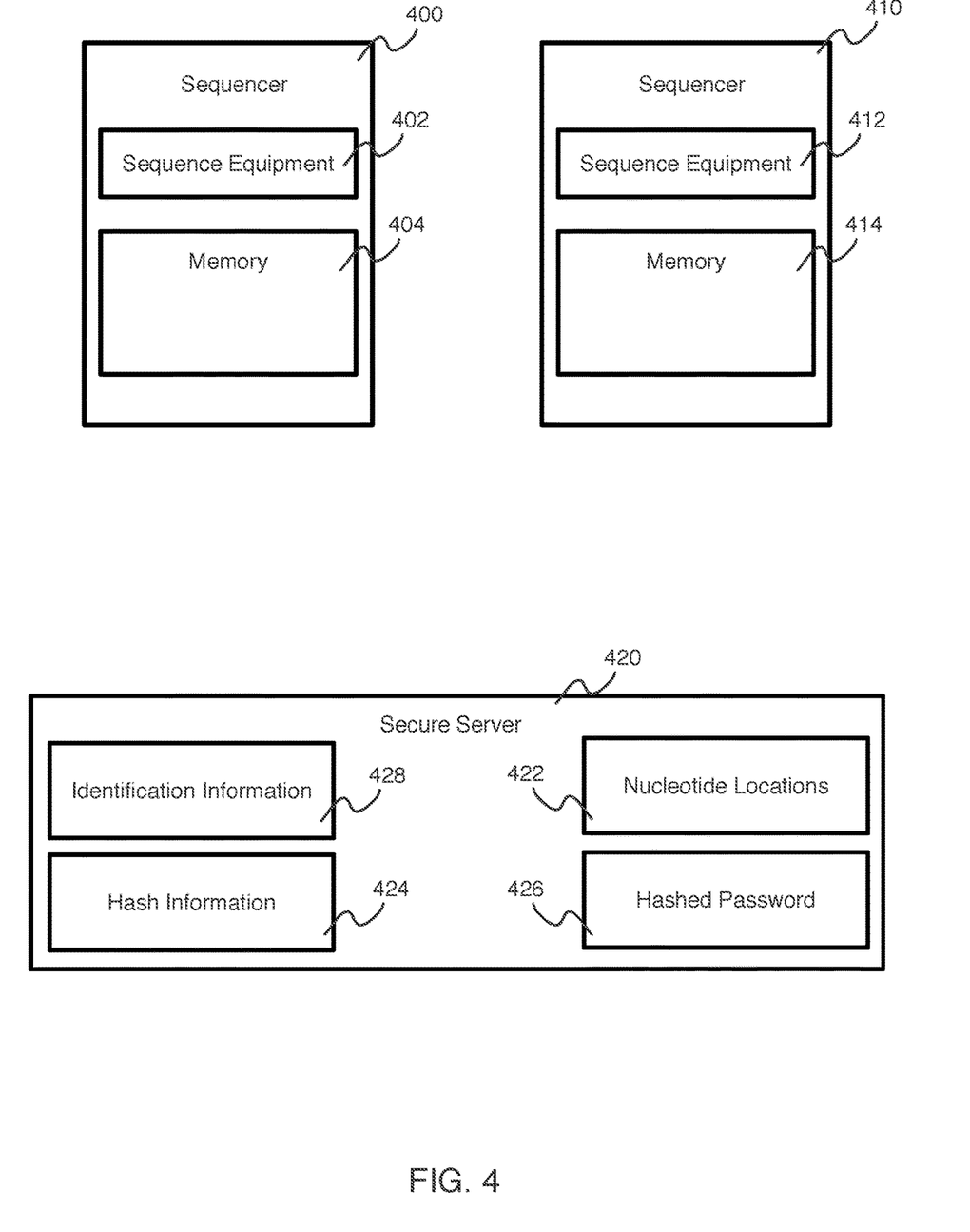
FIG. 4 depicts an example embodiment of a first sequencer, a second sequencer and secure server, in accordance with embodiments with the present disclosure.

In some of the embodiments discussed herein, a sequencer that is part of a secure-consent network communicates with other components of the secure-consent network (e.g., remotely located sequencers or secure servers). FIG. 4 depicts an example embodiment of three such components that may be remotely located. Sequencers 400 and 410 contain sequence equipment 402 and 412. Sequence equipment 402 and 412 may be used by sequencers 400 and 410 to sequence DNA samples and detect nucleotides at particular nucleotide locations, in accordance with embodiments of the present disclosure. Sequencers 400 and 410 also include memories 404 and 414, in which information pertaining to developing hashed passwords may be stored.

Sequencer 400, for example, may be located locally with a user. Sequencer 400 may be licensed to a medical specialist's office to which a user has been referred by the user's primary-care physician. Sequencer 410, on the other hand, may be licensed to the user's primary-care office. Sequencer 410, therefore, may have previously established a hashed password for the user (for example, through method 100), and sequencer 410 may create a subsequent hashed password (for example, through method 300) to verify against that previously established hashed password.

Sequencers 400 and 410 may be part of a secure-consent network that may license the sequencers to businesses that participate in the secure-consent network. The secure-consent network may also operate secure server 420, which may be located remotely from sequencer 400 and sequencer 410, and may store most information needed by sequencers to create and verify DNA based hashed passwords. For example, secure server 420 contains the user's identification information 428, which may include a user ID and universal unique identifier (sometimes referred to herein as a "UUID"). A user ID, for example, may be carried by the user and used to locate the user's information in a secure-consent network. With the user ID, a sequencer may be able to obtain a UUID for the user, which may enable the sequencer to query a secure server for other information required to verify the user's identity (e.g., nucleotide locations, a hash algorithm, and a cryptographic salt).

In some embodiments, for example, memory 404 and 414 may in sequencers 400 and 410 may only store identification information for the user, and all other information (e.g., nucleotide locations 422, hash information 424, and the previously created hashed password 426) may be stored in the secure server 420 in addition to the user's identification information 428. In this embodiment, sequencer 400 may discard all information related to hashed password 426 after creating it and transmitting it to secure server 400 except for the user's identification information. This may be beneficial, for example, to avoid multiple copies of sensitive information being stored in multiple locations. In these embodiments, sequencers 400 and 410 may individually, or together, transmit the user's identification information to secure server 420 when attempting to create further hashed passwords for the user or verify a hashed password for the user.

Figure 5:
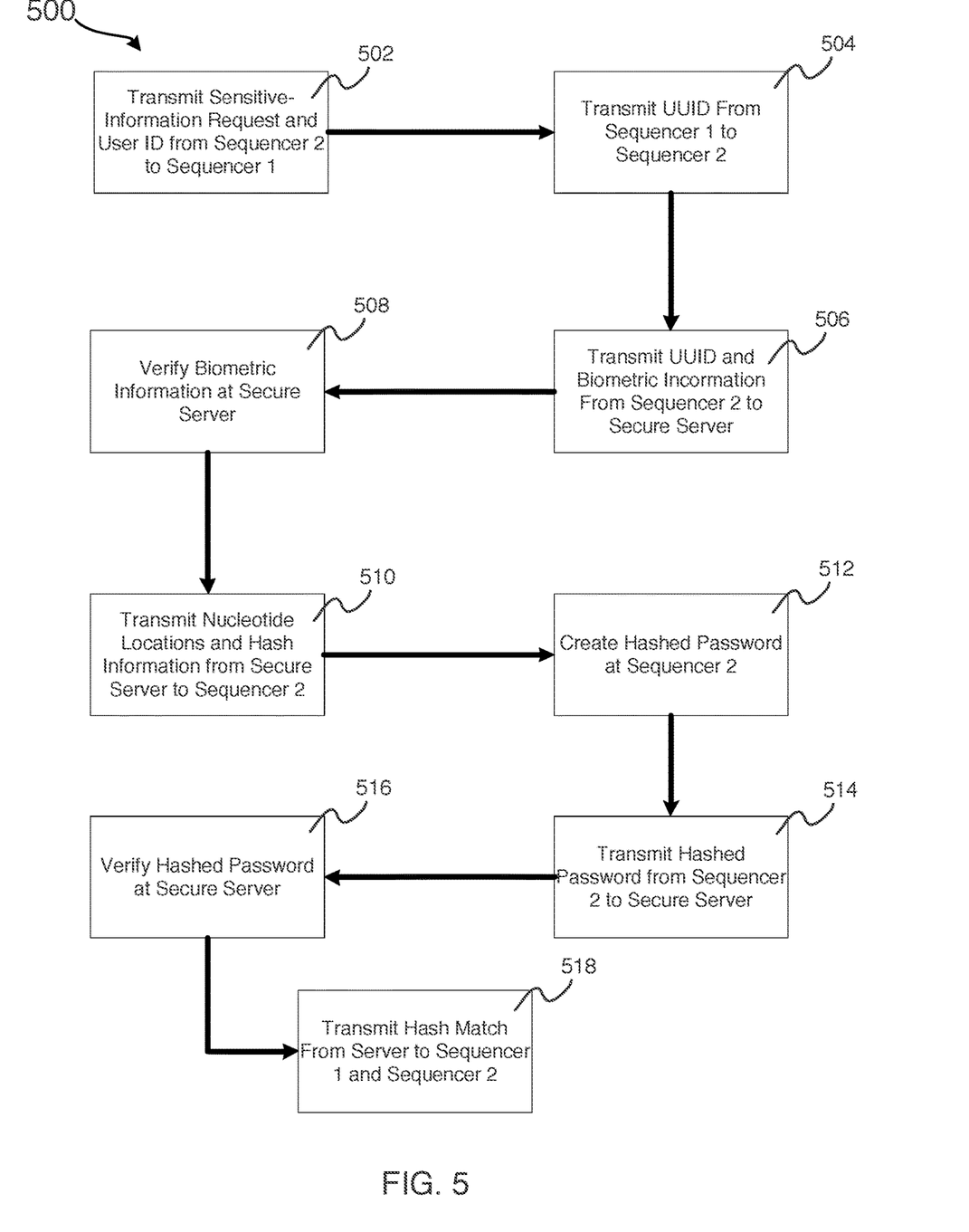
FIG. 5 depicts a method of securely providing user consent to transfer sensitive information using DNA-based hashed passwords, in accordance with embodiments with the present disclosure.

FIG. 5 depicts a method 500 of securely providing user consent to transfer sensitive information using DNA based hashed passwords. Method 500 includes securely determining whether a hashed password established by a first sequencer matches a subsequent hashed password established by a second sequencer. Method 500 includes both a user ID and a unique universal identifier in a way that decreases the likelihood that method 500 could be used to fraudulently transfer sensitive information. Method 500 may be performed by a secure consent network that includes a first sequencer at a first location (e.g., a first medical office), a second sequencer at a second location (e.g., a second medical office), and a secure server at a third location (e.g., a storage facility operated by the secure consent network).

In some embodiments, the first sequencer and second sequencer may be licensed to the first and second locations, but may still be owned by the secure consent network. In some of these embodiments, the sequencers may largely operate without significant intervention of the third parties at the first and second locations (e.g., employees of the first and second medical offices) to increase user anonymity. For example, in some embodiments the sequencer at the second location may only allow the input of (1) information that identifies the first location (e.g., by searching through a secure-consent network contact list), (2) input of a user ID, (3) input of a DNA sample, and (4) nature of the sensitive-information request. With those four inputs, the second sequencer, first sequencer, and secure server may operate autonomously.

Method begins in block 502 in which the second sequencer transmits a sensitive-information request and a user ID to the first sequencer. The user ID may be, for example, a user account name, such as a log-in ID. In some embodiments, the user ID may be maintained in a system to which the second sequencer has access. For example, the sequencer may be able to query a secure server requesting the secure server to transmit the user ID associated with the user's name. Alternatively, the user ID may be provided by the user. In some embodiments, this user ID may have been established for the user by sequencer 1 when sequencer 1 was creating the previously created hashed password for the user. In other embodiments, this user ID may have been established for the user by a secure server when the user signed up for the secure-consent service.

When sequencer 1 receives the sensitive-information request and user ID, sequencer 1 locates a unique universal indicator associated with sequencer 2. This unique universal identifier may connect the user with one of more previously created hashed passwords and the associated nucleotide locations and hash information. In some embodiments, this UUID may be unique for the user ID and previously created hashed password. For example, the user may have a single user ID, but a new UUID may be created each time a new hashed password is created for the user. Thus, if the user's dentist and financial planner both participate in the secure-consent network, the user may use the same user ID with the dentist and financial planner, but the UUID created for the user at the dentist may be different than the UUID that is created for the user at the financial planner.

The UUID is transmitted from sequencer 1 to sequencer 2 in block 504. In block 506, the UUID is transmitted from sequencer 2 to the secure server. The secure server may, for example, operate a database that contains a profile for the user. In some embodiments, the database may contain the user ID, the UUID, nucleotide locations, previously created hashed passwords, and hash information. Sequencer 2 may also transmit the user's biometric information to the secure server. For example, sequencer 2 may scan the user's retina or fingerprint prior to transmitting the user's UUID to the secure server.

In block 508 the secure server may verify that the biometric information transmitted at block 506 matches the biometric information stored in the secure server and associated with that UUID. In some embodiments, this may be beneficial, for example, to verify that the person submitting the user ID to sequencer 2 is indeed the user and not, for example, an identity thief.

Once the biometric information is verified in block 508, the secure server transmits, in block 510, the nucleotide locations and hash information associated with the user ID to sequencer 2. Sequencer 2 then creates a hashed password for the user at block 512 using the nucleotide locations and hash information received in block 510. The hashed password may be created using a DNA sample obtained from the user by, for example, the methods disclosed by FIG. 1, 2, or 3. Sequencer 2 may then transmit the hashed password to the secure server for verification in block 514. The secure server may then compare the hashed password to a previously created hashed password associated with that UUID in block 516. When the hashed password is verified, the secure server may transmit a hash-match notification to sequencer 1 and 2 in block 518. Once sequencer 1 receives the hash-match notification, the organization licensing sequencer 1 may fulfill the sensitive-information request and send the requested information to the organization licensing sequencer 2.

It is noteworthy that, in some embodiments discussed herein, certain actions were described as being performed by a "sequencer." Except where inconsistent with a particular embodiment, a sequencer could take several different forms in those embodiments. For example, in some embodiments a sequencer may take the form of a hand-held device that is capable of accepting DNA samples, biometric readings, and communicate with other sequencers or secure servers. In other embodiments, a sequencer may take the form of a desktop computer with equipment attached thereto for DNA sequencing functions. In yet other embodiments, a sequencer may take the form of a program or other piece of software loaded onto a desktop computer or server with equipment attached thereto for DNA sequencing functions.

Figure 6:
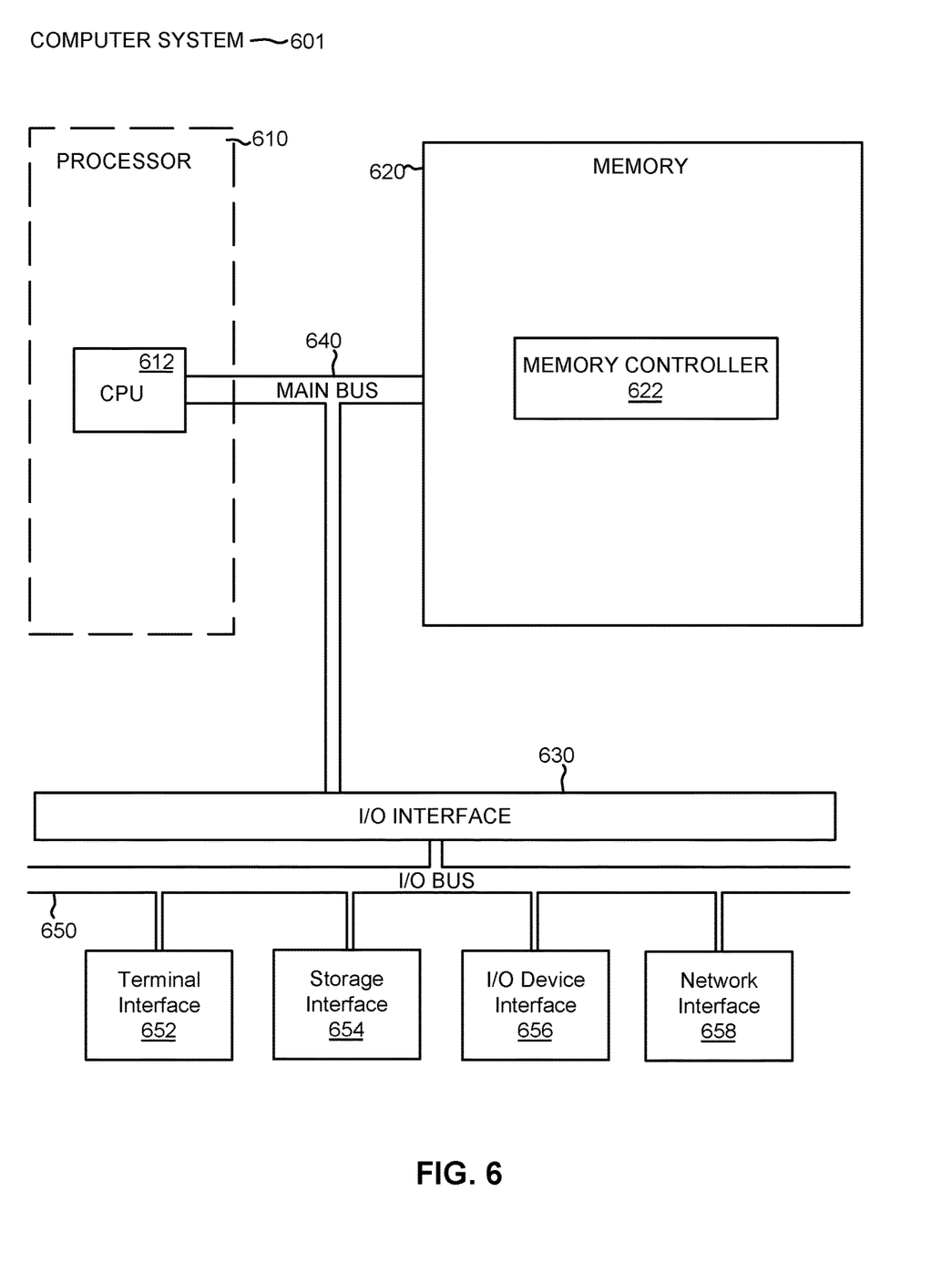
FIG. 6 depicts the representative major components of a computer system that may be used in accordance with embodiments.

FIG. 6 depicts the representative major components of an example Computer System 601 that may be used in accordance with embodiments of the present disclosure. The particular components depicted are presented for the purpose of example only and are not necessarily the only such variations. The Computer System 601 may include a Processor 610, Memory 620, an Input/Output Interface (also referred to herein as I/O or I/O Interface) 630, and a Main Bus 640. The Main Bus 640 may provide communication pathways for the other components of the Computer System 601. In some embodiments, the Main Bus 640 may connect to other components such as a specialized digital signal processor (not depicted).

The Processor 610 of the Computer System 601 may include one or more CPUs 612. The Processor 610 may additionally include one or more memory buffers or caches (not depicted) that provide temporary storage of instructions and data for the CPU 612. The CPU 612 may perform instructions on input provided from the caches or from the Memory 620 and output the result to caches or the Memory 620. The CPU 612 may include one or more circuits configured to perform one or methods consistent with embodiments of the present disclosure. In some embodiments, the Computer System 601 may contain multiple Processors 610 typical of a relatively large system. In other embodiments, however, the Computer System 601 may be a single processor with a singular CPU 612.

The Memory 620 of the Computer System 601 may include a Memory Controller 622 and one or more memory modules for temporarily or permanently storing data (not depicted). In some embodiments, the Memory 620 may include a random-access semiconductor memory, storage device, or storage medium (either volatile or non-volatile) for storing data and programs. The Memory Controller 622 may communicate with the Processor 610, facilitating storage and retrieval of information in the memory modules. The Memory Controller 622 may communicate with the I/O Interface 630, facilitating storage and retrieval of input or output in the memory modules. In some embodiments, the memory modules may be dual in-line memory modules.

The I/O Interface 630 may include an I/O Bus 650, a Terminal Interface 652, a Storage Interface 654, an I/O Device Interface 656, and a Network Interface 658. The I/O Interface 630 may connect the Main Bus 640 to the I/O Bus 650. The I/O Interface 630 may direct instructions and data from the Processor 610 and Memory 620 to the various interfaces of the I/O Bus 650. The I/O Interface 630 may also direct instructions and data from the various interfaces of the I/O Bus 650 to the Processor 610 and Memory 620. The various interfaces may include the Terminal Interface 652, the Storage Interface 654, the I/O Device Interface 656, and the Network Interface 658. In some embodiments, the various interfaces may include a subset of the aforementioned interfaces (e.g., an embedded computer system in an industrial application may not include the Terminal Interface 652 and the Storage Interface 654).

Logic modules throughout the Computer System 601—including but not limited to the Memory 620, the Processor 610, and the I/O Interface 630—may communicate failures and changes to one or more components to a hypervisor or operating system (not depicted). The hypervisor or the operating system may allocate the various resources available in the Computer System 601 and track the location of data in Memory 620 and of processes assigned to various CPUs 612. In embodiments that combine or rearrange elements, aspects of the logic modules' capabilities may be combined or redistributed. These variations would be apparent to one skilled in the art.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

---

---

What is claimed is:

1. A method comprising:
    determining a password-length threshold, wherein the password-length threshold comprises an integer;
    obtaining, for a user, a set of nucleotide locations, wherein a number of nucleotide locations in the set is greater than or equal to the integer;
    obtaining a first sample of the user's DNA;
    determining, in the first sample, a nucleotide at each nucleotide location in the set of nucleotide locations, resulting in a first nucleotide-password sequence; and
    performing a one-way hashing operation on the first nucleotide-password sequence with a first hashing algorithm, resulting in a first hashed password.

2. The method of claim 1, further comprising storing the first hashed password, the set of nucleotide locations, and the first hashing algorithm in a profile for the user.

3. The method of claim 2, further comprising:
    obtaining a second sample of the user's DNA;
    obtaining, from the user profile, the set of nucleotide locations and the first hashing algorithm;
    determining, in the second sample, a nucleotide at each nucleotide location in the set of nucleotide locations, resulting in a second nucleotide-password sequence;
    performing the one-way hashing operation on the second nucleotide-password sequence with the first hashing algorithm, resulting in a second hashed password;
    comparing the first hashed password to the second hashed password; and
    concluding, based on the comparing, that the first hashed password matches the second hashed password.

4. The method of claim 1, wherein the obtaining the set of nucleotide locations and the first hashing algorithm further comprises:
    transmitting, to a first third party, identification information for the user;
    receiving, from the first third party, a universally unique identifier (UUID); and
    retrieving, using the UUID, the set of nucleotide locations and the first hashing algorithm.

5. The method of claim 1, wherein the set of nucleotide locations comprises locations of known single nucleotide polymorphisms.

6. The method of claim 1, wherein the set of nucleotide locations comprises a set of locations of known cytosine-guanine sequences, and the determining comprises identifying, for each location of known cytosine-guanine sequences in the set of locations of known cytosine-guanine sequences, methylation of the corresponding cytosine nucleotide.

7. The method of claim 3, wherein obtaining the first sample of DNA comprises recording a biometric signature of the user, wherein obtaining the second sample of DNA comprises re-recording the biometric signature of the user, and wherein the method further comprises determining that the recorded biometric signature and the re-recorded biometric signature match.

8. The method of claim 1, wherein performing the one-way hashing operation comprises inputting a cryptographic salt to the first hashing algorithm.

9. A system comprising a first sequencer, the first sequencer comprising:
a processor; and
a memory in communication with the processor, the memory containing program instructions that, when executed by the processor, are configured to cause the sequencer to perform a first method, the first method comprising:
obtaining, a password-length threshold wherein the password-length threshold comprises an integer;
obtaining, for a first user, a set of nucleotide locations, wherein a number of nucleotide locations in the set is greater than or equal to the integer;
obtaining a first sample of the user's DNA;
determining, in the first sample, a nucleotide at each nucleotide location in the set of nucleotide locations, resulting in a first nucleotide-password sequence; and
performing a one-way hashing operation on the first nucleotide-password sequence with a first hashing algorithm, resulting in a first hashed password.

10. The system of claim 9, wherein the first method further comprises:
transmitting the first hashed password to a storage server; and
securely deleting the first hashed password, the set of nucleotide locations, and the first hashing algorithm.

11. The system of claim 10, the system further comprising the storage server, the storage server configured to perform a second method, the second method comprising:
receiving, from the first sequencer, the first hashed password; and
storing, in a profile for the user, the first hashed password, the set of nucleotide locations, and the first hashing algorithm.

12. The system of claim 11, further comprising a second sequencer, the second sequencer configured to perform a third method, the third method comprising:
transmitting user identification information for the user to the storage server;
obtaining, from the storage server, the set of nucleotide locations and first hashing algorithm;
obtaining a second sample of the user's DNA;
determining, in the second sample, a nucleotide at each nucleotide location in the set of nucleotide locations, resulting in a second nucleotide-password sequence;

performing the one-way hashing operation on the first second nucleotide-password sequence with the first hashing algorithm, resulting in a second hashed password; and
transmitting the second hashed password to the storage server.

13. The system of claim 12, wherein the second method also comprises:
receiving, from the second sequencer, the second hashed password;
verifying that the first hashed password matches the second hashed password; and
transmitting, as a result of the verifying, a hash match to the first sequencer and the second sequencer.

14. The system of claim 12, wherein the first method further comprises:
receiving, from the second sequencer, a request for sensitive information associated with the first user; and
transmitting, to the second sequencer, a universally unique ID associated with the first user.

15. The system of claim 10, wherein the first method further comprises querying the storage server for the set of nucleotide locations.

16. The system of claim 10, wherein the first method further comprises querying the storage server for the first hashing algorithm.

17. A computer program product, the computer program product comprising a computer readable storage medium having program instructions embodied therewith, the program instructions executable by a computer to cause the computer to:
receive, from a first sequencer, identification information associated with a first user;
transmit, to the first sequencer, a set of nucleotide locations and a set of hash information, wherein each nucleotide location is one nucleotide in length;
receive, from the first sequencer, a first hashed password; and
storing, in a profile for the first user, the set of nucleotide locations, the set of hash information, the identification information, and the hashed password.

18. The computer program product of claim 17, wherein the program instructions are further executable by the computer to cause the computer to:
receive, from the first sequencer, a second hashed password;
verify that the first hashed password and the second hashed password match; and
send a hash-match notification to the first sequencer.

19. The computer program product of claim 17, wherein the program instructions are further executable by the computer to cause the computer to:
receive, from a second sequencer, the identification information;
transmit, to the second sequencer, the set of nucleotide locations and the set of hash information;
receive, from the second sequencer, a third hashed password;
verify that the first hashed password and the third hashed password match; and
send a hash-match notification.

20. The computer program product of claim 19, wherein the hash-match notification is sent to the first sequencer.

* * * * *